(12) United States Patent
Bangert et al.

(10) Patent No.: US 12,146,175 B2
(45) Date of Patent: Nov. 19, 2024

(54) METHOD FOR PRODUCING A RECOMBINANT BACTERIAL COLLAGEN-LIKE PROTEIN (CLP)

(71) Applicant: Evonik Operations GmbH, Essen (DE)

(72) Inventors: Christian Bangert, Linsengericht (DE); Steffen Oßwald, Nidderau (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 18/682,024

(22) PCT Filed: Aug. 3, 2022

(86) PCT No.: PCT/EP2022/071829
§ 371 (c)(1),
(2) Date: Feb. 7, 2024

(87) PCT Pub. No.: WO2023/016892
PCT Pub. Date: Feb. 16, 2023

(65) Prior Publication Data
US 2024/0263211 A1   Aug. 8, 2024

(30) Foreign Application Priority Data
Aug. 9, 2021 (EP) .................................... 21190336

(51) Int. Cl.
| | | |
|---|---|---|
| C12N 1/20 | (2006.01) | |
| C07K 14/78 | (2006.01) | |
| C12N 1/14 | (2006.01) | |
| C12N 15/63 | (2006.01) | |
| C12P 21/02 | (2006.01) | |

(52) U.S. Cl.
CPC .................................... C12P 21/02 (2013.01)

(58) Field of Classification Search
CPC ........... C12N 15/63; C12N 1/14; C07K 14/78
See application file for complete search history.

(56) References Cited

U.S. PATENT DOCUMENTS

| | | | |
|---|---|---|---|
| 5,275,940 A | 1/1994 | Kino et al. | |
| 5,756,345 A | 5/1998 | Camakaris et al. | |
| 5,770,409 A | 6/1998 | Pfefferle et al. | |
| 5,827,698 A | 10/1998 | Kikuchi et al. | |
| 5,990,350 A | 11/1999 | Stevens et al. | |
| 6,150,081 A * | 11/2000 | Van Heerde ........... | C07K 14/78 430/569 |
| 7,138,266 B2 | 11/2006 | Debabov et al. | |

FOREIGN PATENT DOCUMENTS

| | | |
|---|---|---|
| WO | 02/04615 | 1/2002 |
| WO | 2004/094615 | 11/2004 |
| WO | 2007/012078 | 1/2007 |
| WO | 2009/043803 | 4/2009 |
| WO | 2010/091251 | 8/2010 |
| WO | 091251 * | 8/2010 |
| WO | 2014/146175 | 9/2014 |
| WO | 2015/031950 | 3/2015 |
| WO | 2023/016890 | 2/2023 |
| WO | 2023/016895 | 2/2023 |

OTHER PUBLICATIONS

U.S. Appl. No. 18/682,348, filed Feb. 8, 2024.
U.S. Appl. No. 18/682,010, filed Feb. 7, 2024.
U.S. Appl. No. 18/692,970, filed Mar. 18, 2024, Weber et al.
Báez et al., "Recombinant microbial systems for the production of human collagen and gelatin", Appl Microbiol Biotechnol, vol. 69, Oct. 21, 2005, pp. 245-252.
International Search Report received for PCT Application No. PCT/EP2022/071829, mailed on Jan. 2, 2023, 9 pages.
Lukomski et al., "Collagen-like proteins of pathogenic streptococci", Molecular Microbiology, vol. 103, Jan. 18, 2017, pp. 919-930.
Peng et al., "A simple cost-effective methodology for large-scale purification of recombinant non-animal collagens", Appl Microbiol Biotechnol, vol. 98, Jan. 9, 2014, pp. 1807-1815.
Written Opinion received for PCT Application No. PCT/EP2022/071829, mailed on Jan. 2, 2023, 10 pages.
Yoshizumi et al., "Designed Coiled Coils Promote Folding of a Recombinant Bacterial Collagen", The Journal of Biological Chemistry, vol. 286, No. 20, May 20, 2011, pp. 17512-17520.
Yu et al., "Noncollagenous region of the streptococcal collagen-like protein is a trimerization domain that supports refolding of adjacent homologous and heterologous collagenous domains", Protein Science, vol. 19, Feb. 16, 2010, pp. 775-785.
Yu et al., "Dissecting a Bacterial Collagen Domain from *Streptococcus pyogenes*", The Journal of Biological Chemistry, vol. 286, No. 21, May 27, 2011, pp. 18960-18968.
Yu et al., "Bacterial collagen-like proteins that form triple-helical structures", Journal of Structural Biology, vol. 186, Jan. 14, 2014, pp. 451-461.

* cited by examiner

*Primary Examiner* — Maryam Monshipouri
(74) *Attorney, Agent, or Firm* — Grüneberg and Myers PLLC (57) ABSTRACT

A method for producing a recombinant collagen-like protein (CLP) can be performed. The method includes fermenting a host cell, accumulating the CLP in a medium to obtain a fermentation broth, separating the host cell from the fermentation broth to obtain a supernatant, and incubating the supernatant. The CLP can be purified after incubation.

12 Claims, 4 Drawing Sheets
Specification includes a Sequence Listing.

METHOD FOR PRODUCING A RECOMBINANT BACTERIAL COLLAGEN-LIKE PROTEIN (CLP)

CROSS-REFERENCE TO RELATED APPLICATIONS

This application is a National Stage entry under § 371 of International Application No. PCT/EP2022/071829, filed on Aug. 3, 2022, and which claims the benefit of priority to European Patent Application No. 21190336.4, filed on Aug. 9, 2021. The content of each of these applications is hereby incorporated by reference in its entirety.

REFERENCE TO A SEQUENCE LISTING

The present application is accompanied by an XML file as a computer readable form containing the sequence listing entitled, "005907US-seqlist-as-filed.xml", created on Jan. 31, 2024, with a file size of 11,261 bytes, the content of which is hereby incorporated by reference in its entirety.

BACKGROUND OF THE INVENTION

Field of the Invention

The present invention relates to a novel method for producing a recombinant collagen-like protein (CLP). More specifically, the invention concerns the In vitro folding of the Scl2 protein sequence forming a triple helical structure in absence of a V-domain which has never been observed up to now and actual conditions which are crucial for proper folding of the Scl2 protein into a triple helical structure.

Description of Related Art

Collagen-like proteins (CLPs) of bacterial origin (the most industrially relevant being the product of *Streptococcus pyogenes*) have considerably interesting mechanical properties, similar to those of higher eukaryotes' collagen proteins, without needing the complex maturing steps required for the eukaryotic counterparts. CLPs present a common structure: two alpha helixes, stabilizing each other, constitute a "V domain", which is followed by a rod-like, structural collagen domain (CL). After the collagen domain, typically a membrane anchor (GPI-like) is present at the C-terminal end of the protein.

As described in various publications (Lukomski et al. 2002, Brodsky et al. 2009) the current understanding of this process is that the V-domain is required for folding three Scl2 protein monomers into one triple helical structure in vitro (Lukomski et al. reveals in vivo folding without V-domain).

Expression of collagen-like proteins have been attempted in several systems, including *Escherichia coli* and *Saccharomyces cerevisiae*. This invention focuses on expression optimization and purification of *Streptococcus pyogenes* CLP in different hosts.

For expression in *E. coli* the construct of choice for such production carries a specific and necessary modification, in order to efficiently remove the potentially immunogenic V domain: such modification consists of a protease cleavage site typically inserted between the V domain and the collagen sequence. Due to this modification, the protein produced by the bacterial host must be extracted from the intracellular fraction and processed with a specific protease to remove the V domain. The mature protein, consisting of only the collagen-like domain, must be purified against the cleaved V domain, the whole intracellular protein content and the protease added to process the immature CLP. Such workflow greatly hinders the cost-effectiveness of the whole process, due to 1) the product of choice must be separated from the whole content of expression host cells, and 2) proteases are typically expensive enzymes.

Therefore, it was an objective of the present invention to provide an improved process for the production and purification of CLP, which is cost-effective and is applicable without the need to add specific proteases for cleavage of the domain.

This invention provides a solution to achieve a much more cost-effective process, using an industrial workhorse like the yeast *Pichia pastoris*. *Pichia pastoris* has been used as a host for other classes of collagen molecules, typically of mammalian origin, as recently reported by Werten and colleagues (Biotechnology Advances 37, Issue 5, 2019, Pages 642-666); however, the of the use of *P. pastoris* for CLP production has not been described, yet. Moreover, the use of such yeast surprisingly provided a solution to the cleavage of V domain from the mature protein.

In order to understand if the presence of the V domain could be the reason why secreted expression is so inefficient, such domain has been analyzed using a recently published X-ray structure (J. Biol. Chem. 289, 5122-5133), complemented by manual evaluation using a publicly available tool, JPred (compbio.dundee.ac.uk/ipred). It has been possible to identify the structural determinants of the V domain: this domain has been previously reported to be essential for collagen folding in the vast majority of scientific publications (Protein Science 2010, vol. 19, pp 775-785; J. Biol. Chem., Vol. 280, No. 19, pp. 19343-19349, among many others), although the implication of V domain presence on protein expression has ever being discussed or mentioned. Yu et al. analyzed the role of different fragments of scl2 bacterial subunits (J. Biol. Chem. 286, pp. 18960-18968) in contest of collagen stability, limiting the observation to the structural region but generating also fragments devoid of V domain. Here, no report on improvement of production level is mentioned: this is not surprising, since it is argued that the effect observed as a result of the truncation of V domain is exercised when collagen is secreted, which is an undescribed process for bacterial collagen so far.

Following this hypothesis, a series of truncation were generated: the underlying logic was to maintain a part of V domain, generally reported to be essential for collagen folding, reducing its sequence to minimize any disturbance to the production machinery within the cell, and so being able to secrete significant amount of protein in the supernatant. Upon cloning and introduction of these constructs in *P. pastoris* and other hosts, surprisingly it was realized that secretion of CLPs was greatly improved when the V domain was truncated from the original complete sequence. Partial removal of the V domain allowed to significantly increase protein production in all hosts surprisingly, complete removal of the V domain was not as efficient as partial truncation of such domain.

Even though the V-domain might have a positive effect on this process it was found that it's not the sole factor for folding the protein. It could be shown that a proper folding also takes place in absence of the V-domain. The main factors identified are concentration of the Scl2 monomer, temperature, time, pH-value und salt concentration.

Since the V-domain was thought to be crucial for production of triple helical Scl2 it was never considered to remove this sequence leading to the following challenges:

The V-domain makes up for approximately one third of the whole sequence and hinders the protein to be transported out of the *Pichia pastoris* host. This requires a complex downstream process containing cell lysis to remove the target protein from the cell.

The V-domain itself has pathogenic properties and needs to be removed during the purification process. This is done by a protease digest. Usage of a protease is quite costly, and it needs to be removed during downstream as well.

The following summary shows the process steps required for a product purification using a Scl2 construct with V-domain attached:
Cell separation (Centrifugation)
Cell lysis (Pressure homogenizer)
V-domain removal (Protease digest)
Removal of cell debris (pH-shift, centrifugation)
Purification (Solvent precipitation)
Washing (TFF)
Further purification (IEX)
Such a process is disclosed in Peng et al. (Appl. Microbiol. Biotechnol., 98:1807-1815, 2014) for example.

This invention describes a novel process to produce collagen-like proteins (CLPs) in the methylotrophic yeast *Pichia pastoris* or other hosts. The key features of such process, compared to the current process known from the prior art: 1) proteins are secreted in culture supernatant, allowing to reach a high titer (>5 g/L), in a low-cost medium; 2) proteins are easily purified from the supernatant, since no complex component is present in the cultivation medium.

Surprisingly, the purified product from supernatants of *Pichia pastoris* cultivation secreting Scl2p, showed an unexpected profile, compatible with mature collagen-like sequences. Further analysis showed how intracellular enzymes, most likely the processing protease Kex2p, are capable to remove the V domain protein sequence without any need of an additional protease step. In addition, in order to modify a cleavage site present in the final product, resulting in significant accumulation of degradation products, the protein sequence has been mutated to engineer such cleavage site and abolish degradation. Unexpectedly, the most efficient performance was obtained when an apolar amino acid (valine, in the wild-type sequence) was mutated to a polar amino acid (glutamine).

It was a surprising finding that the recombinant CLP could after secretion in the culture supernatant be correctly folded in absence of the V-domain during storage/freezing of the cell pellet before lysis. With the present invention a new downstream process is disclosed, including production of the Scl2 protein without V-domain and the intentional integration of a folding step for the CL domain.

Therefore, the invention provides a novel method for producing a recombinant collagen-like protein (CLP) comprising the following steps:
a) fermentation of a host cell, expressing a CLP with an amino acid sequence that is at least 60% identical to the amino acid sequence of SEQ ID NO:1, in a medium, wherein the amino acid sequence comprises a deletion of at least 38 amino acids at the N-terminus of the amino acid sequence of SEQ ID NO:1,
b) accumulation of the CLP in the medium, wherein a fermentation broth is obtained,
c) separating the host cells from the fermentation broth to obtain a supernatant,
d) incubating the supernatant of fermentation broth of step c) for at least 1 h at not more than 25° C. for folding of the CLP,
e) optionally purification of the CLP by at least one of the following: solvent precipitation, tangential flow filtration (TFF), ion exchange chromatography, reversed-phase chromatography.

The host cell is preferably selected from bacterial, yeast of plant cells. It is preferred to use bacterial or yeast cells.

It was a surprising finding that truncated variants of the collagen-like protein, including variants with a truncated V-domain or without any V-domain lead to increased production of collagen-like protein and secretion into the fermentation medium. It was further surprising that the truncated variants could be correctly folded in absence of the V-domain.

SUMMARY OF THE INVENTION

It is preferred, when the amino acid sequence comprises a deletion of between 38 and 90 amino acids at the N-terminus of the amino acid sequence of SEQ ID NO:1. This includes a complete deletion of the N-terminal V-domain (comprising 74 amino acids) and different truncations of the V-domain of at least 38 amino acids.

In a preferred embodiment, the amino acid sequence that is at least 60%, identical to the amino acid sequence of SEQ ID NO:2, SEQ ID NO:3, SEQ ID NO:4, SEQ ID NO:5, SEQ ID NO:6, SEQ ID NO:7, SEQ ID NO:8 or SEQ ID NO:9.

In a preferred configuration the amino acid sequence is at least 90%, 92%, 94%, 96%, 97%, 98%, 99% or 100%, preferably 97%, particularly preferably 98%, very particularly preferably 99%, and extremely preferably 100%, identical to the amino acid sequence of SEQ ID NO:2, SEQ ID NO:3, SEQ ID NO:4, SEQ ID NO:5, SEQ ID NO:6, SEQ ID NO:7, SEQ ID NO:8 or SEQ ID NO:9.

In a preferred embodiment of the present invention the CLP is a bacterial collagen-like protein from *Streptococcus pyogenes*.

The invention correspondingly also relates to polypeptide variants of SEQ ID NO:2 to 9, which contain one or more insertion(s) or deletion(s). Preferably, the polypeptide contains a maximum of 5, a maximum of 4, a maximum of 3, or a maximum of 2, insertions or deletions of amino acids.

In a preferred embodiment the folding of CLP in step d) is performed at a temperature between −80° C. and 25° C., preferably between 0° C. and 20° C. In a preferred configuration folding is performed in presence of glycerin or salts.

In another preferred embodiment, folding of CLP in step d) is performed for a time between 1 h and 48 h, preferably between 1 h and 24 h.

In another preferred embodiment, folding of CLP in step d) is performed with a concentration of CLP of at least 1 mg/ml, preferably at least 4 mg/ml.

In a preferred embodiment, the host cell is a microorganism of the species *P. pastoris, E. coli, P. putida* or *C. glutamicum* comprising any of the polypeptides according to the present invention.

In a preferred embodiment, the microorganism is a yeast of the genus *P. pastoris* or a bacterial cell, preferably *E. coli, Corynebacterium* or *Brevibactetium*.

The microorganism may be a microorganism in which the nucleotide sequence is present in overexpressed form.

The microorganism may be characterized in that the microorganism has the capability of producing and secreting a fine chemical. The fine chemical being preferably a collagen-like protein.

Overexpression is taken to mean, generally, an increase in the intracellular concentration or activity of a ribonucleic acid, a protein (polypeptide) or an enzyme, compared with the starting strain (parent strain) or wild-type strain, if this is the starting strain. A starting strain (parent strain) is taken to mean the strain on which the measure leading to the overexpression was carried out.

In the overexpression, the methods of recombinant overexpression are preferred. These include all methods in which a microorganism is produced using a DNA molecule provided in vitro. Such DNA molecules comprise, for example, promoters, expression cassettes, genes, alleles, encoding regions etc. These are converted into the desired microorganism by methods of transformation, conjugation, transduction or like methods.

The extent of the expression or overexpression can be established by measuring the amount of the mRNA transcribed by the gene, by determining the amount of the polypeptide, and by determining the enzyme activity.

The culture medium or fermentation medium that is to be used must appropriately satisfy the demands of the respective strains. Descriptions of culture media of various microorganisms are contained in the handbook "Manual of Methods for General Bacteriology" of the American Society for Bacteriology (Washington D.C., USA, 1981). The terms culture medium and fermentation medium or medium are mutually exchangeable.

As carbon source, sugars and carbohydrates can be used, such as, e.g., glucose, sucrose, lactose, fructose, maltose, molasses, sucrose-containing solutions from beet sugar or sugar cane processing, starch, starch hydrolysate and cellulose, oils and fats, such as, for example, soybean oil, sunflower oil, groundnut oil and coconut fat, fatty acids, such as, for example, palmitic acid, stearic acid and linoleic acid, alcohols such as, for example, glycerol, methanol and ethanol, and organic acids, such as, for example, acetic acid or lactic acid.

As nitrogen source, organic nitrogen compounds such as peptones, yeast extract, meat extract, malt extract, cornsteep liquor, soybean meal and urea or inorganic compounds such as ammonium sulphate, ammonium chloride, ammonium phosphate, ammonium carbonate and ammonium nitrate can be used. The nitrogen sources can be used individually or as a mixture.

As phosphorus source, phosphoric acid, potassium dihydrogenphosphate or dipotassium hydrogenphosphate or the corresponding sodium-containing salts can be used.

The culture medium must, in addition, contain salts, for example in the form of chlorides or sulphates of metals such as, for example, sodium, potassium, magnesium, calcium and iron, such as, for example, magnesium sulphate or iron sulphate, which are necessary for growth. Finally, essential growth substances such as amino acids, for example homoserine and vitamins, for example thiamine, biotin or pantothenic acid, can be used in addition to the above-mentioned substances.

Said starting materials can be added to the culture in the form of a single batch or supplied in a suitable manner during the culturing.

Basic compounds such as sodium hydroxide, potassium hydroxide, ammonia or ammonia water, or acid compounds such as phosphoric acid or sulphuric acid, are used in a suitable manner for pH control of the culture. The pH is generally adjusted to 6.0 to 8.5, preferably 6.5 to 8. For control of foam development, antifoams can be used, such as, for example, polyglycol esters of fatty acids. For maintaining the stability of plasmids, suitable selectively acting substances such as, for example, antibiotics, can be added to the medium. The fermentation is preferably carried out under aerobic conditions. In order to maintain said aerobic conditions, oxygen or oxygen-containing gas mixtures such as, for example, air, are introduced into the culture. The use of liquids that are enriched with hydrogen peroxide is likewise possible. Optionally, the fermentation is carried out at superatmospheric pressure, for example at a superatmospheric pressure of 0.03 to 0.2 MPa. The temperature of the culture is usually 20° C. to 45° C., and preferably 25° C. to 40° C., particularly preferably 30° C. to 37° C. In the case of batch or fed-batch processes, the culturing is preferably continued until an amount sufficient for the measure of obtaining the desired organic chemical compound has formed. This goal is usually reached within 10 hours to 160 hours. In continuous processes, longer culture times are possible. Owing to the activity of the microorganisms, enrichment (accumulation) of the fine chemicals in the fermentation medium and/or in the cells of the microorganisms occurs.

Examples of suitable fermentation media may be found, inter alia, in patent documents U.S. Pat. Nos. 5,770,409, 5,990,350, 5,275,940, WO 2007/012078, U.S. Pat. No. 5,827,698, WO 2009/043803, U.S. Pat. No. 5,756,345 or U.S. Pat. No. 7,138,266; appropriate modifications may optionally be carried out to the requirements of the strains used.

The process may be characterized in that it is a process which is selected from the group consisting of batch process, fed-batch process, repetitive fed-batch process and continuous process.

The process may be further characterized in that the fine chemical or a liquid or solid fine chemical-containing product is obtained from the fine chemical-containing fermentation broth.

The performance of the processes or fermentation processes according to the invention with respect to one or more of the parameters selected from the group of concentration (compound formed per volume), yield (compound formed per carbon source consumed), volumetric productivity (compound formed per volume and time) and biomass-specific productivity (compound formed per cell dry mass or bio dry mass and time or compound formed per cell protein and time) or other process parameters and combinations thereof, is increased by at least 0.5%, at least 1%, at least 1.5% or at least 2%, based on processes or fermentation processes with microorganisms in which the promoter variant according to the invention is present.

Owing to the measures of the fermentation, a fermentation broth is obtained which contains the desired fine chemical, preferably amino acid or organic acid.

Then, a product in liquid or solid form that contains the fine chemical is provided or produced or obtained.

A fermentation broth is taken to mean, in a preferred embodiment, a fermentation medium or nutrient medium in which a microorganism was cultured for a certain time and at a certain temperature. The fermentation medium, or the media used during the fermentation, contains/contain all substances or components that ensure production of the desired compound and typically ensure growth and/or viability.

On completion of the fermentation, the resultant fermentation broth accordingly contains
 a) the biomass (cell mass) of the microorganism resulting from growth of the cells of the microorganism,
 b) the desired fine chemical formed in the course of the fermentation, c) the organic by-products possibly formed in the course of the fermentation, and d) the components of the fermentation medium used, or of the starting materials, that are not consumed by the fermentation, such as, for example, vitamins such as biotin, or salts such as magnesium sulphate.

The organic by-products include substances which are generated in addition to the respective desired compound by the microorganisms used in the fermentation and are possibly secreted.

The fermentation broth is withdrawn from the culture vessel or the fermentation container, optionally collected, and used for providing a product in liquid or solid form containing the fine chemical. The expression "obtaining the fine chemical-containing product" is also used therefor. In the simplest case, the fine chemical-containing fermentation broth withdrawn from the fermentation container is itself the product obtained.

By way of one or more of the measures selected from the group a) partial (>0% to <80%) to complete (100%) or virtually complete (≥80%, ≥90%, ≥95%, ≥96%, ≥97%, ≥98%, ≥99%) removal of the water, b) partial (>0% to <80%) to complete (100%) or virtually complete (≥80%, ≥90%, ≥95%, ≥96%, ≥97%, ≥98%, ≥99%) removal of the biomass, wherein this is optionally inactivated before the removal, c) partial (>0% to <80%) to complete (100%) or virtually complete (≥80%, ≥90%, ≥95%, ≥96%, ≥97%, ≥98%, ≥99%, ≥99.3%, ≥99.7%) removal of the organic by-products formed in the course of the fermentation, and d) partial (>0%) to complete (100%) or virtually complete (≥80%, ≥90%, ≥95%, ≥96%, ≥ 97%, ≥98%, ≥99%, ≥99.3%, ≥99.7%) removal of the components of the fermentation medium used or the starting materials that are not consumed by the fermentation, a concentration or purification of the desired organic chemical compound is achieved from the fermentation broth. In this manner, products are isolated that have a desired content of the compound.

The partial (>0% to <80%) to complete (100%) or virtually complete (≥80% to <100%) removal of the water (measure a)) is also termed drying.

In a variant of the process, by complete or virtually complete removal of the water, the biomass, the organic by-products and the non-consumed components of the fermentation medium used, pure (≥ 80% by weight, ≥90% by weight) or high-purity (>95% by weight, ≥97% by weight, ≥99% by weight) product forms of the desired organic chemical compound, preferably collagen-like protein, are successfully arrived at. For the measures according to a), b), c) or d), a great variety of technical instructions are available in the prior art.

In the case of processes for producing collagen-like protein processes are preferred in which products are obtained that do not contain any components of the fermentation broth. These products are used, in particular, in human medicine, in the pharmaceuticals industry, and in the food industry.

EXAMPLES

The collagen-like protein was produced in the yeast host cell *Pichia pastoris* by fermentation. To produce Scl2 from *Streptococcus pyogenes* in *Pichia pastoris*, the sequence of the collagen-like protein (full-length protein and truncated variants and no-V-domain variant), has been codon optimized using different algorithms, and cloned in a secretion vector for *Pichia pastoris*. The sequences used are summarized in SEQ ID NO:1 to SEQ ID NO:9. For each of the specific sequences, a vector was transformed in *Pichia pastoris* following standard protocol and a standard expression protocol in fed-batch mode was applied (Damasceno, L. M., Huang, C J. & Batt, C. A. *Protein secretion in Pichia pastoris and advances in protein production. Appl Microbiol Biotechnol* 93, 31-39 (2012)). The collagen domain of the Scl2p protein was detected via HPLC analysis in the supernatant of cell culture. Upon fermentation, supernatant has been separated from biomass via centrifugation (12000 g, 5 mins at room temperature).

The collagen domain of the Scl2p protein based on the sequences SEQ ID NO:1 to SEQ ID NO:9 could be produced under similar conditions using either *E. coli, B. choshinensis* or *C. glutamicum*. In case of a production in yeast or *C. glutamicum*, the collagen domain is secreted by the cell. No cell lysis is needed as an initial purification step in this approach. In case of a production in *E. coli* a cell lysis is mandatory to remove the collagen domain from the cell.

The full-length collagen-like protein, a truncated variant (truncation 3) and the no-V-domain variant (based on the gene scl2 from *Streptococcus pyogenes*) were also expressed in *Brevibacillus choshinensis*. Therefore, the corresponding DNA sequences were cloned into a suitable secretion vector for *B. choshinensis*. Transformation of *B. choshinensis* with the new constructed plasmids was done according to Mizukami et al. 2010 (Curr Pharm Biotechnol 2010, 13:151-258).

The *B. choshinensis* strains were analyzed for their ability to produce the different collagen-like proteins in batch cultivations at 33° C. and pH 7 using the DASGIP® parallel bioreactor system from Eppendorf (Hamburg, Germany). The fermentation was performed using 1 L reactors. The production medium (TM medium, Biomed Res Int 2017, 2017: 5479762) contained 10 g/L glucose. Upon fermentation, supernatant has been separated from biomass by centrifugation and was used for SDS PAGE analysis. For all three variants, collagen domain of the Scl2p protein was produced.

The full-length collagen-like protein and the no-V-domain variant (based on the gene scl2 from *Streptococcus pyogenes*) were also expressed in *Corynebacterium glutamicum*. Therefore, the corresponding DNA sequences were cloned together with an upstream located signal peptide for protein secretion into a shuttle vector for *C. glutamicum* (Biotechnology Techniques 1999, 13: 437-441). The *C. glutamicum* strain ATCC 13032 was transformed with the new constructed plasmids by means of electroporation as described by Ruan et al. (Biotechnology Letters 2015, 37: 2445-2452).

The *C. glutamicum* strains were analyzed for their ability to produce the different collagen proteins in fed-batch cultivations at 30° C. and pH 7 using the DASGIP® parallel bioreactor system from Eppendorf (Hamburg, Germany). The fermentation was performed using 1 L reactors. The production medium contained 20 g/L glucose in the batch phase and the fed-batch phase was run with a glucose feed of 4 g/L*h. Upon fermentation, supernatant has been separated from biomass by centrifugation and was used for HPLC analysis. For both variants, collagen domain of the Scl2p protein was produced. For the truncated variant of the collagen-like protein, titer was higher as for the full-length variant.

The process steps are summarized below:
1. Production of collagen-like protein in yeast, *E. coli* or *Corynebacterium*

2. Cell lysis (only for *E. coli*)
3. Cell separation (Filtration or centrifugation)
4. Folding of the CL single strand to form a triple helical structure
5. Further purification by solvent precipitation and ultra-filtration
6. Freeze dry of the purified CL protein

DETAILED DESCRIPTION OF THE INVENTION

Figure 1:
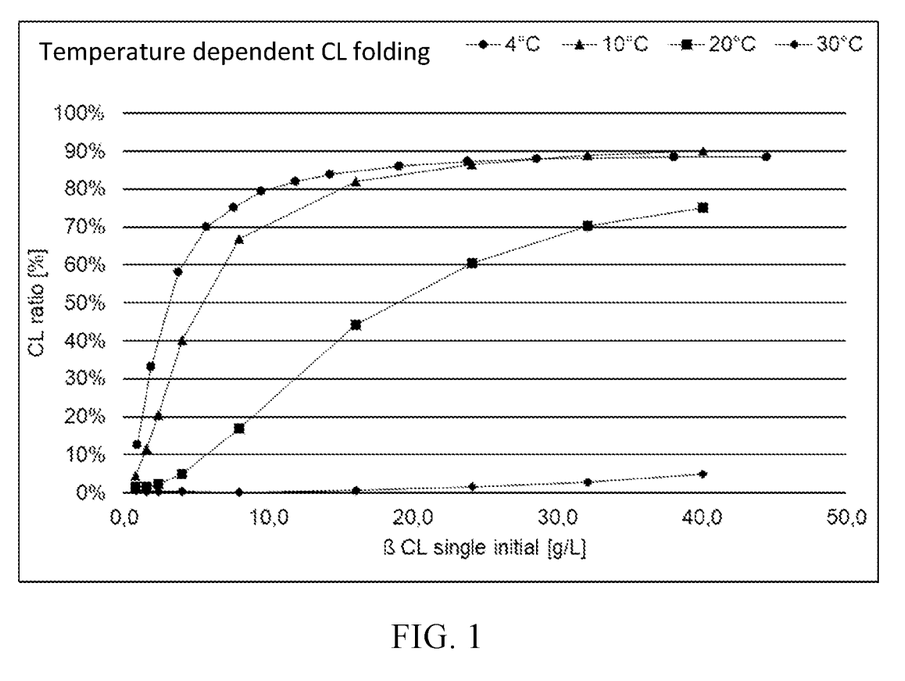
FIG. 1 shows the temperature dependent folding of the collagen-like protein.

To determine folding kinetics, freeze dried collagen domain of the Scl2p protein coming from a production in *Pichia pastoris* is dissolved at a concentration of 40 g/L in DI water and unfolded at 40° C. The solution is split up and further diluted in a concentration range from 1-40 g/L. The different samples are then incubated at different temperatures ranging from 4-30° C. for 20 h to obtain a folding kinetic of collagen-like protein in the temperature and concentration range given. The folding rate is determined using Size exclusion chromatography (SEC). The temperature dependent folding of the collagen-like protein is summarized in FIG. 1.

Figure 2:
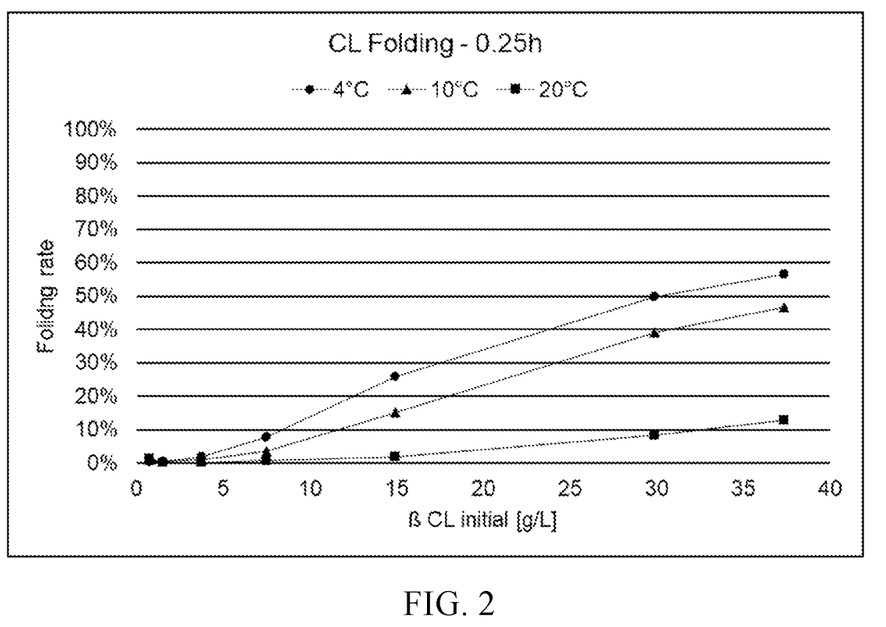
FIG. 2 shows the time dependent folding of the CL protein in a time range of 0.25 h and an incubation temperature of 4-20° C.
Figure 3:
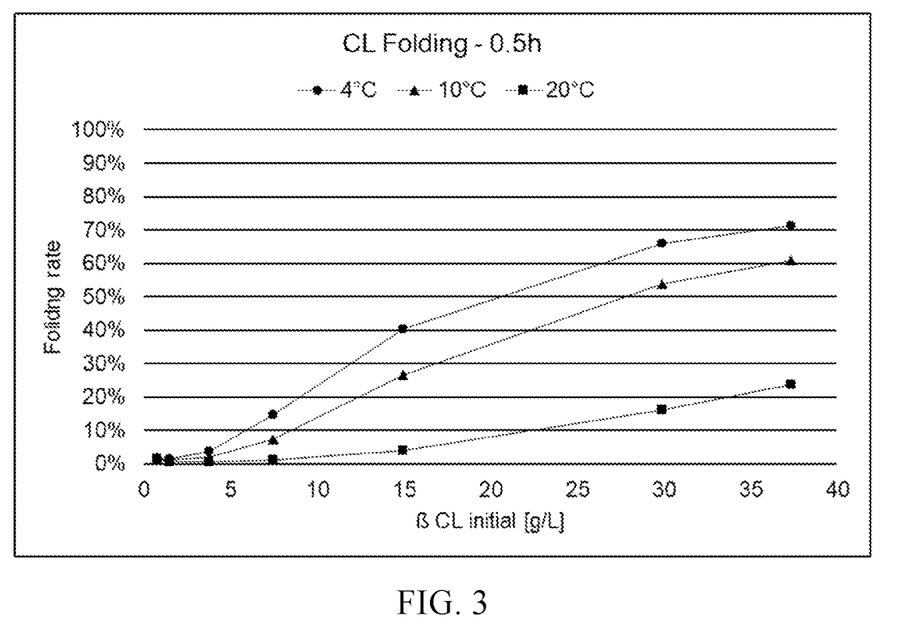
FIG. 3 shows the time dependent folding of the CL protein in a time range of 0.5 h and an incubation temperature of 4-20° C.
Figure 4:
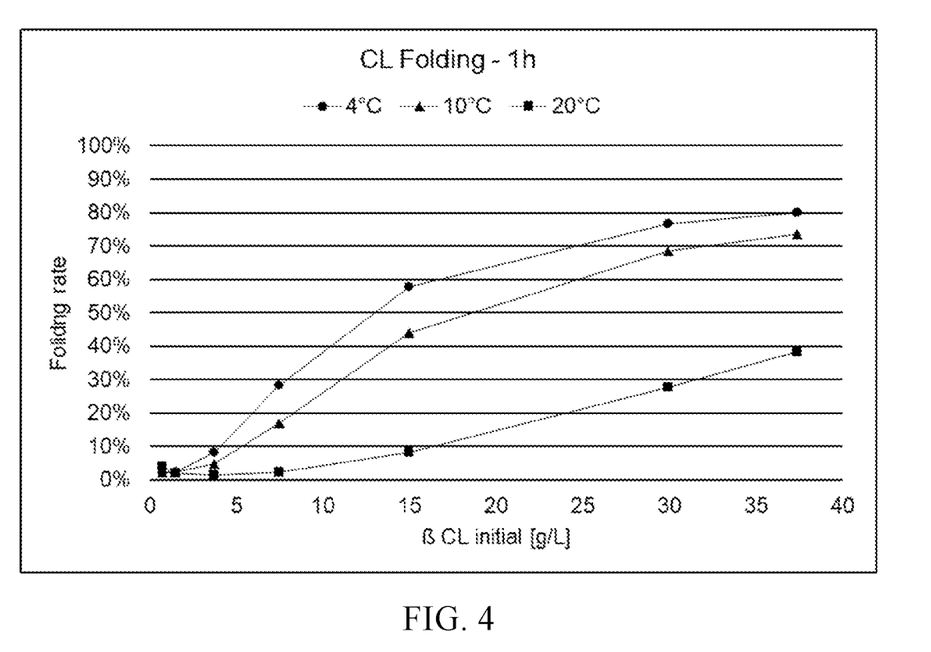
FIG. 4 shows the time dependent folding of the CL protein in a time range of 1 h and an incubation temperature of 4-20° C.

A second sample set is prepared to cover time dependent folding of the CL protein in a time range of 0.25-1 h and an incubation temperature of 4-20° C. The results are summarized in FIGS. 2 to 4.

Protein Sequences
SEQ ID NO:1 *Streptococcus pyogenes* Collagen-like protein (CLP), full length protein
SEQ ID NO:2 *Streptococcus pyogenes* CLP, truncation 3
SEQ ID NO:3 *Streptococcus pyogenes* CLP, truncation 5
SEQ ID NO:4 *Streptococcus pyogenes* CLP, no V-domain
SEQ ID NO:5 *Streptococcus pyogenes* CLP, truncation 5 (AGPR mutant)
SEQ ID NO:6 *Streptococcus pyogenes* CLP, truncation 5 (QGPR mutant)
SEQ ID NO:7 *Streptococcus pyogenes* CLP, truncation 5 (VGPA mutant)
SEQ ID NO:8 *Streptococcus pyogenes* CLP, truncation 5 (SGPR mutant)
SEQ ID NO:9 *Streptococcus pyogenes* CLP, truncation 5 (VGPK mutant)

The invention claimed is:

1. A method for producing a recombinant collagen-like protein (CLP), the method comprising:
   a) fermenting at least one host cell, expressing a CLP with an amino acid sequence that is at least 90% identical to the amino acid sequence of SEQ ID NO:2, SEQ ID NO:3, SEQ ID NO:4, SEQ ID NO:5, SEQ ID NO: 6, SEQ ID NO:7, SEQ ID NO:8 or SEQ ID NO:9, in a medium, wherein the amino acid sequence comprises a deletion of at least 38 amino acids at the N-terminus of the amino acid sequence of SEQ ID NO:1,
   b) accumulating the CLP in the medium, wherein a fermentation broth is obtained,
   c) separating the at least one host cell from the fermentation broth to obtain a supernatant,
   d) incubating the supernatant of the fermentation broth of c) for at least 1 h at a temperature between 0° C. and 20° C. for folding of the CLP, e) optionally purifying the CLP by at least one selected from the group consisting of: solvent precipitation, tangential flow filtration (TFF), ion exchange chromatography, and reversed-phase chromatography, wherein said at least one host cell is at least one host cell selected from the group consisting of *Pichia pastoris*, *Brevibacillus choshinensis*, *Corynebacterium glutamicum* and *Escherichia coli*.

2. The method according to claim 1, wherein the amino acid sequence comprises a deletion of between 38 and 90 amino acids at the N-terminus of the amino acid sequence of SEQ ID NO:1.

3. The method according to claim 1, wherein the CLP is a collagen-like protein from *Streptococcus pyogenes*.

4. The method according to claim 1, wherein the folding of the CLP in d) is performed for a time between 1 h and 48 h.

5. The method according to claim 1, wherein the folding of the CLP in d) is performed with a concentration of the CLP of at least 1 mg/ml.

6. The method according to claim 1, wherein the amino acid sequence is 100% identical to the amino acid sequence of SEQ ID NO:2, SEQ ID NO:3, SEQ ID NO: 4, SEQ ID NO:5, SEQ ID NO:6, SEQ ID NO:7, SEQ ID NO:8 or SEQ ID NO:9.

7. The method according to claim 1, wherein the amino acid sequence is 97% identical to the amino acid sequence of SEQ ID NO:2, SEQ ID NO:3, SEQ ID NO: 4, SEQ ID NO:5, SEQ ID NO:6, SEQ ID NO:7, SEQ ID NO:8 or SEQ ID NO:9.

8. The method according to claim 1, wherein the amino acid sequence is 98% identical to the amino acid sequence of SEQ ID NO:2, SEQ ID NO:3, SEQ ID NO: 4, SEQ ID NO:5, SEQ ID NO:6, SEQ ID NO:7, SEQ ID NO:8 or SEQ ID NO:9.

9. The method according to claim 1, wherein the amino acid sequence is 99% identical to the amino acid sequence of SEQ ID NO:2, SEQ ID NO:3, SEQ ID NO: 4, SEQ ID NO:5, SEQ ID NO:6, SEQ ID NO:7, SEQ ID NO:8 or SEQ ID NO:9.

10. The method according to claim 1, wherein the folding of the CLP in d) is performed for a time between 1 h and 24 h.

11. The method according to claim 1, wherein the folding of the CLP in d) is performed with a concentration of the CLP of at least 4 mg/ml.

12. The method according to claim 1, wherein said at least one host cell is *Pichia pastoris*.

* * * * *

```
                          SEQUENCE LISTING

Sequence total quantity: 9
SEQ ID NO: 1           moltype = AA  length = 330
FEATURE                Location/Qualifiers
source                 1..330
                       mol_type = protein
                       organism = Streptococcus pyogenes
SEQUENCE: 1
NHKVHMHHHH HHADEQEEKA KVRTELIQEL AQGLGGIEKK NFPTLGDEDL DHTYMTKLLT   60
YLQEREQAEN SWRKRLLKGI QDHALDLVPR GSPGLPGPRG EQGPTGPTGP AGPRGLQGLQ  120
GLQGERGEQG PTGPAGPRGL QGERGEQGPT GLAGKAGEAG AKGETGPAGP QGPRGEQGPQ  180
GLPGKDGEAG AQGPAGPMGP AGERGEKGEP GTQGAKGDRG ETGPVGPRGE RGEAGPAGKD  240
GERGPVGPAG KDGQNGQDGL PGKDGKDGQN GKDGLPGKDG KDGQNGKDGL PGKDGKDGQD  300
GKDGLPGKDG KDGLPGKDGK DGQPGKPGKY                                  330

SEQ ID NO: 2           moltype = AA  length = 292
FEATURE                Location/Qualifiers
source                 1..292
                       mol_type = protein
                       organism = Streptococcus pyogenes
SEQUENCE: 2
NHKVHMHHHH HHDHTYMTKL LTYLQEREQA ENSWRKRLLK GIQDHALDLV PRGSPGLPGP   60
RGEQGPTGPT GPAGPRGLQG LQGLQGERGE QGPTGPAGPR GLQGERGEQG PTGLAGKAGE  120
AGAKGETGPA GPQGPRGEQG PQGLPGKDGE AGAQGPAGPM GPAGERGEKG EPGTQGAKGD  180
RGETGPVGPR GERGEAGPAG KDGERGPVGP AGKDGQNGQD GLPGKDGKDG QNGKDGLPGK  240
DGKDGQNGKD GLPGKDGKDG QDGKDGLPGK DGKDGLPGKD GKDGQPGKPG KY          292

SEQ ID NO: 3           moltype = AA  length = 267
FEATURE                Location/Qualifiers
source                 1..267
                       mol_type = protein
                       organism = Streptococcus pyogenes
SEQUENCE: 3
NHKVHMHHHH HHLLKGIQDH ALDLVPRGSP GLPGPRGEQG PTGPTGPAGP RGLQGLQGLQ   60
GERGEQGPTG PAGPRGLQGE RGEQGPTGLA GKAGEAGAKG ETGPAGPQGP RGEQGPQGLP  120
GKDGEAGAQG PAGPMGPAGE RGEKGEPGTQ GAKGDRGETG PVGPRGERGE AGPAGKDGER  180
GPVGPAGKDG QNGQDGLPGK DGKDGQNGKD GLPGKDGKDG QNGKDGLPGK DGKDGQDGKD  240
GLPGKDGKDG LPGKDGKDGQ PGKPGKY                                     267

SEQ ID NO: 4           moltype = AA  length = 240
FEATURE                Location/Qualifiers
source                 1..240
```

```
                        mol_type = protein
                        organism = Streptococcus pyogenes
SEQUENCE: 4
GSPGLPGPRG  EQGPTGPTGP  AGPRGLQGLQ  GLQGERGEQG  PTGPAGPRGL  QGERGEQGPT   60
GLAGKAGEAG  AKGETGPAGP  QGPRGEQGPQ  GLPGKDGEAA  AQGPAGPMGP  AGERGEKGEP  120
GTQGAKGDRG  ETGPVGPRGE  RGEAGPAGKD  GERGPVGPAG  KDGQNGQDGL  PGKDGKDGQN  180
GKDGLPGKDG  KDGQNGKDGL  PGKDGKDGQD  GKDGLPGKDG  KDGLPGKDGK  DGQPGKPGKY  240

SEQ ID NO: 5           moltype = AA   length = 267
FEATURE                Location/Qualifiers
source                 1..267
                       mol_type = protein
                       organism = Streptococcus pyogenes
SEQUENCE: 5
NHKVHMHHHH  HHLLKGIQDH  ALDLVPRGSP  GLPGPRGEQG  PTGPTGPAGP  RGLQGLQGLQ   60
GERGEQGPTG  PAGPRGLQGE  RGEQGPTGLA  GKAGEAGAKG  ETGPAGPQGP  RGEQGPQGLP  120
GKDGEAGAQG  PAGPMGPAGE  RGEKGEPGTQ  GAKGDRGETG  PAGPRGERGE  AGPAGKDGER  180
GPVGPAGKDG  QNGQDGLPGK  DGKDGQNGKD  GLPGKDGKDG  QNGKDGLPGK  DGKDGQDGKD  240
GLPGKDGKDG  LPGKDGKDGQ  PGKPGKY                                         267

SEQ ID NO: 6           moltype = AA   length = 267
FEATURE                Location/Qualifiers
source                 1..267
                       mol_type = protein
                       organism = Streptococcus pyogenes
SEQUENCE: 6
NHKVHMHHHH  HHLLKGIQDH  ALDLVPRGSP  GLPGPRGEQG  PTGPTGPAGP  RGLQGLQGLQ   60
GERGEQGPTG  PAGPRGLQGE  RGEQGPTGLA  GKAGEAGAKG  ETGPAGPQGP  RGEQGPQGLP  120
GKDGEAGAQG  PAGPMGPAGE  RGEKGEPGTQ  GAKGDRGETG  PQGPRGERGE  AGPAGKDGER  180
GPVGPAGKDG  QNGQDGLPGK  DGKDGQNGKD  GLPGKDGKDG  QNGKDGLPGK  DGKDGQDGKD  240
GLPGKDGKDG  LPGKDGKDGQ  PGKPGKY                                         267

SEQ ID NO: 7           moltype = AA   length = 267
FEATURE                Location/Qualifiers
source                 1..267
                       mol_type = protein
                       organism = Streptococcus pyogenes
SEQUENCE: 7
NHKVHMHHHH  HHLLKGIQDH  ALDLVPRGSP  GLPGPRGEQG  PTGPTGPAGP  RGLQGLQGLQ   60
GERGEQGPTG  PAGPRGLQGE  RGEQGPTGLA  GKAGEAGAKG  ETGPAGPQGP  RGEQGPQGLP  120
GKDGEAGAQG  PAGPMGPAGE  RGEKGEPGTQ  GAKGDRGETG  PVGPAGERGE  AGPAGKDGER  180
GPVGPAGKDG  QNGQDGLPGK  DGKDGQNGKD  GLPGKDGKDG  QNGKDGLPGK  DGKDGQDGKD  240
GLPGKDGKDG  LPGKDGKDGQ  PGKPGKY                                         267

SEQ ID NO: 8           moltype = AA   length = 267
FEATURE                Location/Qualifiers
source                 1..267
                       mol_type = protein
                       organism = Streptococcus pyogenes
SEQUENCE: 8
NHKVHMHHHH  HHLLKGIQDH  ALDLVPRGSP  GLPGPRGEQG  PTGPTGPAGP  RGLQGLQGLQ   60
GERGEQGPTG  PAGPRGLQGE  RGEQGPTGLA  GKAGEAGAKG  ETGPAGPQGP  RGEQGPQGLP  120
GKDGEAGAQG  PAGPMGPAGE  RGEKGEPGTQ  GAKGDRGETG  PSGPRGERGE  AGPAGKDGER  180
GPVGPAGKDG  QNGQDGLPGK  DGKDGQNGKD  GLPGKDGKDG  QNGKDGLPGK  DGKDGQDGKD  240
GLPGKDGKDG  LPGKDGKDGQ  PGKPGKY                                         267

SEQ ID NO: 9           moltype = AA   length = 267
FEATURE                Location/Qualifiers
source                 1..267
                       mol_type = protein
                       organism = Streptococcus pyogenes
SEQUENCE: 9
NHKVHMHHHH  HHLLKGIQDH  ALDLVPRGSP  GLPGPRGEQG  PTGPTGPAGP  RGLQGLQGLQ   60
GERGEQGPTG  PAGPRGLQGE  RGEQGPTGLA  GKAGEAGAKG  ETGPAGPQGP  RGEQGPQGLP  120
GKDGEAGAQG  PAGPMGPAGE  RGEKGEPGTQ  GAKGDRGETG  PVGPKGERGE  AGPAGKDGER  180
GPVGPAGKDG  QNGQDGLPGK  DGKDGQNGKD  GLPGKDGKDG  QNGKDGLPGK  DGKDGQDGKD  240
GLPGKDGKDG  LPGKDGKDGQ  PGKPGKY                                         267
```